(12) United States Patent
Fields et al.

(10) Patent No.: US 10,414,408 B1
(45) Date of Patent: *Sep. 17, 2019

(54) REAL-TIME DRIVER MONITORING AND FEEDBACK REPORTING SYSTEM

(71) Applicant: STATE FARM MUTUAL AUTOMOBILE INSURANCE COMPANY, Bloomington, IL (US)

(72) Inventors: Brian Mark Fields, Normal, IL (US); Steve Roberson, Normal, IL (US); Abhishek Harish, Champaign, IL (US); Hyunji Lim, Champaign, IL (US); Matthew James Waughtel, Cuba, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 101 days.

This patent is subject to a terminal disclaimer.

(21) Appl. No.: 15/656,104

(22) Filed: Jul. 21, 2017

Related U.S. Application Data

(63) Continuation of application No. 15/152,790, filed on May 12, 2016, now Pat. No. 9,751,535, which is a
(Continued)

(51) Int. Cl.
*B60W 40/09* (2012.01)
*A61B 5/18* (2006.01)
(Continued)

(52) U.S. Cl.
CPC ............. *B60W 40/09* (2013.01); *A61B 5/18* (2013.01); *B60K 35/00* (2013.01); *B60W 40/08* (2013.01); *G09B 19/14* (2013.01); *G09B 19/167* (2013.01)

(58) Field of Classification Search
None
See application file for complete search history.

(56) References Cited

U.S. PATENT DOCUMENTS 6,636,790 B1  10/2003 Lightner et al.
7,155,321 B2  12/2006 Bromley et al.
(Continued)

OTHER PUBLICATIONS

U.S. Appl. No. 14/494,088, Nonfinal Office Action, dated Dec. 15, 2014.
(Continued)

*Primary Examiner* — Lail A Kleinman
(74) *Attorney, Agent, or Firm* — Marshall, Gerstein & Borun LLP; Randall G. Rueth

(57) ABSTRACT

Real-time feedback may be generated during a driving session from status data collected via one or more sensors. This feedback data may include various metrics related to a student's driving skills, which may be utilized to generate tagged driving events. A user may also manually enter tagged driving events. The tagged driving events may include real-time information based on the collected status data, such as acceleration, braking, cornering data, descriptions entered by the user. The location of these tagged driving events may be mapped in real time. Sensors used to collect this data may be integrated within the device displaying the feedback or located on another device, in which case the status data may be communicated to the device displaying the feedback. The displayed real-time feedback may be viewed by an instructor to assess a student's driving skills in real time and to calculate a driver feedback score.

20 Claims, 6 Drawing Sheets

Related U.S. Application Data continuation of application No. 14/494,251, filed on Sep. 23, 2014, now Pat. No. 9,373,203.

(51) Int. Cl.
  *B60K 35/00* (2006.01)
  *B60W 40/08* (2012.01)
  *G09B 19/14* (2006.01)
  *G09B 19/16* (2006.01)

(56) References Cited

U.S. PATENT DOCUMENTS

| | | |
|---|---|---|
| 7,835,691 B2 | 11/2010 | Groskreutz et al. |
| 7,937,278 B1 | 5/2011 | Cripe et al. |
| 8,140,358 B1 | 3/2012 | Ling et al. |
| 8,306,731 B2 | 11/2012 | Waggaman, III |
| 8,463,488 B1 | 6/2013 | Hart |
| 8,554,468 B1 | 10/2013 | Bullock |
| 8,626,568 B2 | 1/2014 | Warkentin et al. |
| 8,731,768 B2 | 5/2014 | Fernandes et al. |
| 8,738,523 B1 | 5/2014 | Sanchez et al. |
| 8,876,535 B2 | 11/2014 | Fields et al. |
| 8,954,340 B2 | 2/2015 | Sanchez et al. |
| 9,056,616 B1 | 6/2015 | Fields et al. |
| 9,180,888 B1 | 11/2015 | Fields et al. |
| 9,198,206 B2 | 11/2015 | Li et al. |
| 9,279,697 B1 | 3/2016 | Fields et al. |
| 9,315,195 B2 | 4/2016 | Armitage et al. |
| 9,373,203 B1 | 6/2016 | Fields et al. |
| 9,586,591 B1 | 3/2017 | Fields et al. |
| 9,633,252 B2 | 4/2017 | Feng |
| 2002/0181405 A1 | 12/2002 | Ying |
| 2003/0083079 A1 | 5/2003 | Clark et al. |
| 2003/0163587 A1 | 8/2003 | Knight et al. |
| 2003/0195676 A1 | 10/2003 | Kelly et al. |
| 2003/0228005 A1 | 12/2003 | Melick et al. |
| 2004/0054452 A1 | 3/2004 | Bjorkman |
| 2004/0157650 A1 | 8/2004 | Wissinger et al. |
| 2004/0158476 A1 | 8/2004 | Blessinger et al. |
| 2004/0176935 A1 | 9/2004 | Sproule et al. |
| 2004/0236474 A1 | 11/2004 | Chowdhary et al. |
| 2004/0254698 A1 | 12/2004 | Hubbard et al. |
| 2005/0038581 A1 | 2/2005 | Kapolka et al. |
| 2005/0065678 A1 | 3/2005 | Smith et al. |
| 2005/0065679 A1 | 3/2005 | Kawauchi et al. |
| 2005/0091018 A1 | 4/2005 | Craft |
| 2005/0154500 A1 | 7/2005 | Sonnenrein et al. |
| 2005/0165639 A1 | 7/2005 | Ross et al. |
| 2005/0203673 A1 | 9/2005 | El-Hajj et al. |
| 2006/0002842 A1 | 1/2006 | Yoon |
| 2006/0109113 A1 | 5/2006 | Reyes et al. |
| 2006/0247832 A1 | 11/2006 | Taki |
| 2007/0035632 A1 | 2/2007 | Silvernail et al. |
| 2007/0038338 A1 | 2/2007 | Larschan et al. |
| 2007/0038351 A1 | 2/2007 | Larschan et al. |
| 2007/0038352 A1 | 2/2007 | Larschan et al. |
| 2007/0038353 A1 | 2/2007 | Larschan et al. |
| 2007/0050108 A1 | 3/2007 | Larschan et al. |
| 2007/0122771 A1 | 5/2007 | Maeda et al. |
| 2007/0257815 A1 | 11/2007 | Gunderson et al. |
| 2008/0015748 A1 | 1/2008 | Nagy |
| 2008/0064014 A1 | 3/2008 | Wojtczak et al. |
| 2008/0082372 A1 | 4/2008 | Burch |
| 2008/0243558 A1 | 10/2008 | Gupte |
| 2008/0255722 A1 | 10/2008 | McClellan et al. |
| 2009/0069954 A1 | 3/2009 | Aladesuyi |
| 2009/0079555 A1 | 3/2009 | Aguirre De Carcer et al. |
| 2009/0135845 A1 | 5/2009 | Husain et al. |
| 2010/0045452 A1 | 2/2010 | Periwal |
| 2010/0097208 A1 | 4/2010 | Rosing et al. |
| 2010/0174576 A1 | 7/2010 | Naylor |
| 2010/0191411 A1 | 7/2010 | Cook et al. |
| 2010/0210254 A1 | 8/2010 | Kelly et al. |
| 2010/0253508 A1 | 10/2010 | Koen et al. |
| 2010/0256861 A1 | 10/2010 | Hodges |
| 2010/0256864 A1 | 10/2010 | Ying |
| 2011/0009107 A1 | 1/2011 | Guba et al. |
| 2011/0043377 A1 | 2/2011 | McGrath et al. |
| 2011/0125363 A1 | 5/2011 | Blumer et al. |
| 2011/0213628 A1 | 9/2011 | Peak et al. |
| 2011/0251752 A1 | 10/2011 | DeLarocheliere et al. |
| 2011/0254655 A1 | 10/2011 | Maalouf et al. |
| 2011/0276218 A1 | 11/2011 | Dwan et al. |
| 2011/0294466 A1 | 12/2011 | Tang et al. |
| 2011/0307188 A1 | 12/2011 | Peng et al. |
| 2012/0021386 A1 | 1/2012 | Anderson et al. |
| 2012/0041638 A1 | 2/2012 | Johnson et al. |
| 2012/0044052 A1 | 2/2012 | Davis et al. |
| 2012/0046807 A1 | 2/2012 | Ruther et al. |
| 2012/0046825 A1 | 2/2012 | Ruther et al. |
| 2012/0047291 A1 | 2/2012 | Davis et al. |
| 2012/0135382 A1 | 5/2012 | Winston et al. |
| 2012/0215375 A1 | 8/2012 | Chang |
| 2012/0239223 A1 | 9/2012 | Schwarz et al. |
| 2012/0253888 A1 | 10/2012 | Davidson |
| 2012/0303392 A1 | 11/2012 | Depura et al. |
| 2012/0313771 A1 | 12/2012 | Wittliff, III |
| 2013/0006675 A1 | 1/2013 | Bowne et al. |
| 2013/0096731 A1 | 4/2013 | Tamari et al. |
| 2013/0097176 A1 | 4/2013 | Khader et al. |
| 2013/0164715 A1 | 6/2013 | Hunt et al. |
| 2013/0179198 A1 | 7/2013 | Bowne et al. |
| 2013/0184928 A1 | 7/2013 | Kerkhof et al. |
| 2013/0189649 A1 | 7/2013 | Mannino |
| 2013/0209968 A1 | 8/2013 | Miller et al. |
| 2013/0282227 A1 | 10/2013 | Chen et al. |
| 2013/0282228 A1 | 10/2013 | Cawse et al. |
| 2013/0289873 A1 | 10/2013 | Mitchell |
| 2013/0309648 A1 | 11/2013 | Park et al. |
| 2014/0045147 A1 | 2/2014 | Mohn et al. |
| 2014/0058616 A1 | 2/2014 | de Oliveira et al. |
| 2014/0058618 A1 | 2/2014 | Rude et al. |
| 2014/0080098 A1 | 3/2014 | Price |
| 2014/0080100 A1 | 3/2014 | Phelan et al. |
| 2014/0162219 A1 | 6/2014 | Stankoulov |
| 2014/0163848 A1 | 6/2014 | Tamir et al. |
| 2014/0168399 A1 | 6/2014 | Plummer et al. |
| 2014/0189814 A1 | 7/2014 | Marten et al. |
| 2014/0195102 A1 | 7/2014 | Nathanson |
| 2014/0195272 A1 | 7/2014 | Sadiq et al. |
| 2014/0204193 A1 | 7/2014 | Zhang et al. |
| 2014/0257870 A1 | 9/2014 | Cielocha et al. |
| 2014/0266660 A1 | 9/2014 | Slaton et al. |
| 2014/0272810 A1 | 9/2014 | Fields et al. |
| 2014/0309849 A1 | 10/2014 | Ricci |
| 2015/0081162 A1 | 3/2015 | Mitchell et al. |
| 2015/0086953 A1 | 3/2015 | Johansson |
| 2015/0161913 A1 | 6/2015 | Dominguez et al. |
| 2015/0262484 A1 | 9/2015 | Victor et al. |
| 2016/0005332 A1 | 1/2016 | Cale |
| 2017/0132951 A1 | 5/2017 | Fields et al. |

OTHER PUBLICATIONS

U.S. Appl. No. 14/494,088, Notice of Allowance, dated Mar. 30, 2015.
U.S. Appl. No. 14/494,251, filed Sep. 23, 2014.
U.S. Appl. No. 14/494,251, Final Office Action, dated May 12, 2015.
U.S. Appl. No. 14/494,251, Nonfinal Office Action, dated Nov. 13, 2015.
U.S. Appl. No. 14/494,251, Nonfinal Office Action, dated Dec. 5, 2014.
U.S. Appl. No. 14/494,251, Notice of Allowance, dated Apr. 18, 2016.
U.S. Appl. No. 14/699,758, filed Apr. 29, 2015.
U.S. Appl. No. 14/699,758, Final Office Action, dated Feb. 2, 2016.
U.S. Appl. No. 14/699,758, Final Office Action, dated Oct. 21, 2016.
U.S. Appl. No. 14/699,758, Nonfinal Office Action, dated Aug. 17, 2015.
U.S. Appl. No. 14/699,758, Nonfinal Office Action, dated May 25, 2016.

(56) References Cited

OTHER PUBLICATIONS

U.S. Appl. No. 14/702,277, Nonfinal Office Action, dated May 26, 2015.
U.S. Appl. No. 14/702,277, Notice of Allowance, dated Aug. 18, 2015.
U.S. Appl. No. 14/703,482, Final Office Action, dated Dec. 9, 2015.
U.S. Appl. No. 14/703,482, Non-Final Office Action, dated Jul. 1, 2015.
U.S. Appl. No. 14/703,482, Notice of Allowance, dated Jul. 1, 2016.
U.S. Appl. No. 14/703,482, Notice of Allowance, dated Oct. 24, 2016.
U.S. Appl. No. 14/875,826, Nonfinal Office Action, dated Nov. 6, 2015.
U.S. Appl. No. 14/875,826, Notice of Allowance, dated Jan. 7, 2016.
U.S. Appl. No. 15/010,074, filed Jan. 29, 2016.
U.S. Appl. No. 15/010,074, Final Office Action, dated Jun. 8, 2017.
U.S. Appl. No. 15/010,074, Nonfinal Office Action, dated Jan. 13, 2017.
U.S. Appl. No. 15/152,790, Notice of Allowance, dated Jun. 16, 2017.
U.S. Appl. No. 15/152,790, "Real-Time Driver Monitoring and Feedback Reporting System", filed May 12, 2016.

REAL-TIME DRIVER MONITORING AND FEEDBACK REPORTING SYSTEM

CROSS-REFERENCE TO RELATED APPLICATIONS

This application is a continuation of U.S. patent application Ser. No. 15/152,790, which was filed on May 12, 2016, which is a continuation of U.S. patent application Ser. No. 14/494,251, which was filed on Sep. 23, 2014, and issued as U.S. Pat. No. 9,373,203 on Jun. 21, 2016. The disclosure of each is incorporated herein by reference in its entirety.

FIELD OF THE DISCLOSURE

The present disclosure relates to systems, methods, apparatus, and non-transitory computer readable media for use during driving tests, and, more particularly, to using one or more devices to provide real-time driver monitoring and feedback reporting to an instructor regarding a driving test session.

BACKGROUND

Traditionally, a student driver wanting to obtain a drivers' license may take driving classes and/or participate in various driving sessions whereby the student is evaluated on his driving performance. During a typical driving session, a student driver may be requested to drive along a certain route while the student's driving skills are observed and evaluated by an instructor. Based on the instructor's observations, the student driver is graded according to a set of criteria.

BRIEF DESCRIPTION OF THE DRAWINGS

The figures described below depict various aspects of the system and methods disclosed herein. It should be understood that each figure depicts an aspect of a particular aspect of the disclosed system and methods, and that each of the figures is intended to accord with a possible aspect thereof. Further, wherever possible, the following description refers to the reference numerals included in the following figures, in which features depicted in multiple figures are designated with consistent reference numerals.

DETAILED DESCRIPTION

To improve the efficiency and objectivity of the driver testing process, driver monitoring systems may incorporate other sources of data collection in addition to the driver's observations. Using various data collection techniques, one or more computers and/or sensors in the vehicle may record data throughout a driving session. The instructor may then use a report generated from this data to provide feedback to the student and/or to evaluate the student's driving skills once the driving session has ended.

In spite of feedback provided in the generated report, the instructor's role in determining the student's driving skills is important because the instructor may provide valuable feedback to the student during the driving session. In this way, the student may be able to correct problematic driving habits before the driving session has ended and before seeing the driving session report.

Although an instructor may provide the student with feedback during the driving session, this feedback is typically limited to the instructor's physical observations of the student's driving skills, as the instructor does not have access to the collected data until the driving session has ended and the report is generated. Therefore, providing instructors with a way to utilize the collected data in real time to provide students with feedback during a driving session presents several challenges.

Figure 1:
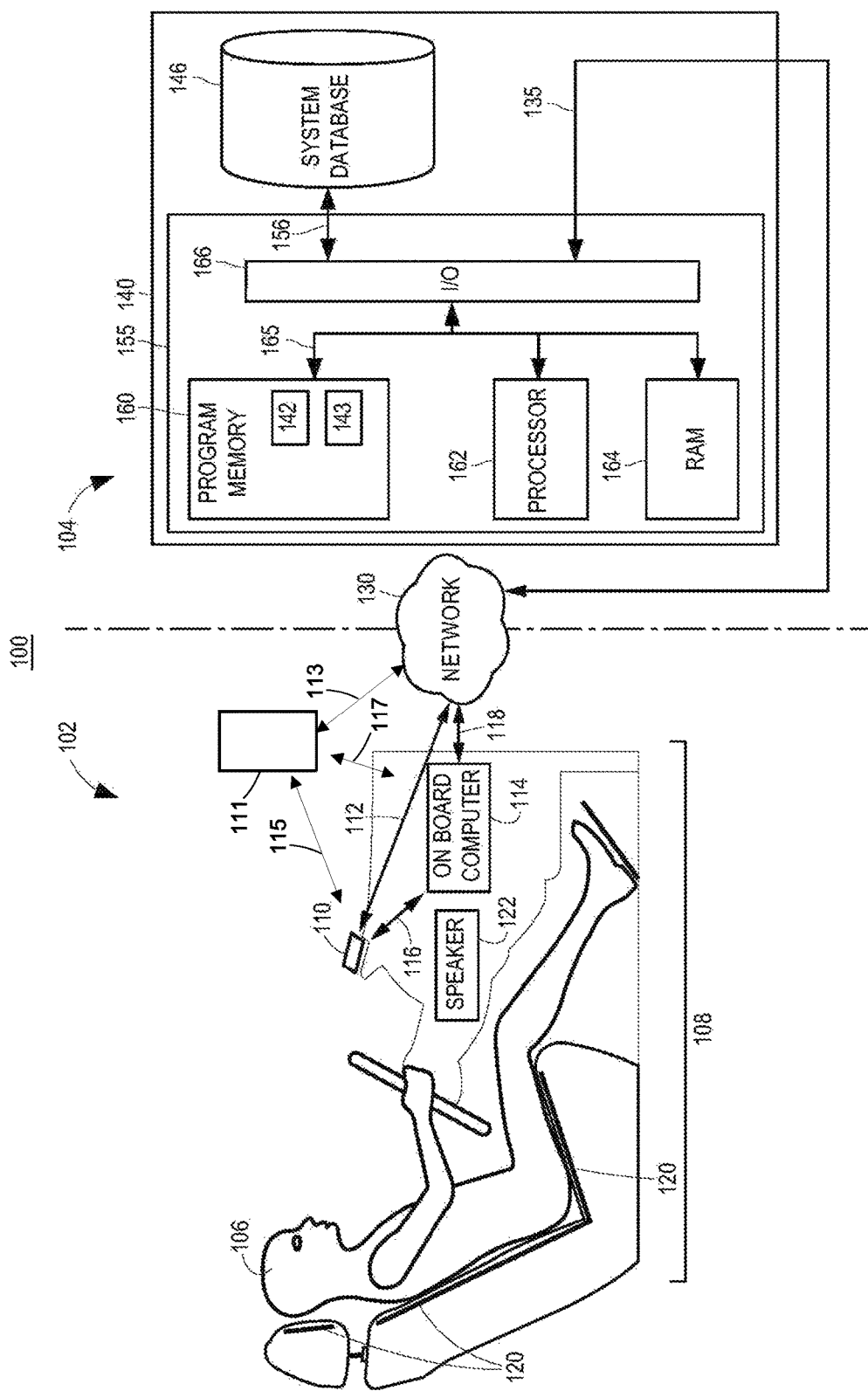
FIG. 1 illustrates a block diagram of an exemplary driver's education evaluation system 100 in accordance with an exemplary aspect of the present disclosure.

I. Collecting Status Data and Displaying Status Metrics During Student Driver Testing FIG. 1 illustrates a block diagram of an exemplary driver's education evaluation system 100 in accordance with an exemplary aspect of the present disclosure. Driver's education evaluation system 100 includes hardware and software applications, as well as various data communication channels for facilitating data communications between the various hardware and software components. Driver's education evaluation system 100 may be divided into front-end components 102 and back-end components 104.

In various aspects, any suitable number of front-end components 102 may be disposed within device 110 and/or device 111. Either of device 110 and/or device 111 may be permanently or removably installed in a vehicle 108 (e.g., a car, truck, etc.). Additionally or alternatively, vehicle 108 may include an on-board computer 114. In various aspects, device 110 and/or device 111 may be implemented as any suitable computing device, such as a smartphone, mobile device, tablet computer, laptop computer, dedicated driver's education evaluation computer, wearable computing device, etc. In an aspect, device 110 may be implemented as a device that has a smaller display than display 111. For example, device 110 may be implemented as a smartphone and device 111 may be implemented as a tablet computer. In this way, a tablet computer device 111 may function as a "digital clipboard" and utilize a larger display screen to display additional information that would otherwise be impractical or difficult to view on a display of smartphone device 110.

In various aspects, device 111 may share one or more functions such that either of device 110, device 111, and/or on-board computer 114 may perform any portion (or all) of the functions performed by the other devices. As will be appreciated by those of ordinary skill in the relevant art(s), functions performed by either device 110, device 111, and/or on-board computer 114 may also be performed by device 110, device 111, and/or on-board computer 114 working in concert with one another.

On-board computer 114 may be permanently installed in vehicle 108 and may interface with various sensors in vehicle 108 (e.g., a braking sensor, a speedometer, a tachometer, etc.) and/or may interface with various external output devices in vehicle 108 such as one or more tactile alert systems 120, one or more speakers 122, one or more displays, etc. A display is not shown in vehicle 108 in FIG. 1 for purposes of brevity. In various aspects, on-board computer 114 may be a general-use on-board computer configured to perform any suitable functions related to vehicle operation and/or may be implemented as a dedicated driver's education evaluation computer. In an aspect, on-board computer 114 may be installed by the manufacturer of vehicle 108 or as an aftermarket modification to vehicle 108, for example. In various aspects, device 110, device 111, and/or on-board computer 114 may be a thin-client device which outsources any suitable portion of processing to server 140 via network 130.

On-board computer 114 may supplement any suitable number of the functions performed by device 110 and/or device 111 described herein by, for example, sending and/or receiving information to and from device 110 and/or device 111. Device 110, device 111, and/or on-board computer 114 may communicate with network 130 over links 112, 113, and 118, respectively. Additionally, device 110, device 111, and/or on-board computer 114 may communicate with one another directly over links 115, 116, and/or 117. Vehicle 108 may also include a tactile alert system 120 (e.g., a seat that can vibrate) that may present tactile alerts to the vehicle operator 106 on command from device 110, device 111, and/or on-board computer 114. While shown in a slightly reclined sitting position, those of ordinary skill in the art will appreciate that the student driver 106 could be situated in any number of ways (e.g., reclining at a different angle, etc.) and operating the vehicle using controls other than the steering wheel and pedals shown in FIG. 1 (e.g., one or more sticks, yokes, levers, etc.).

In various aspects, front-end components 102 may include any suitable combination of hardware and/or software components that are configured to communicate with back-end components 104 via network 130. Network 130 may be any suitable network that facilitates communications between front-end components 102 and back end components 104. Network 130 may include, for example, a proprietary network, a secure public internet, a mobile-based network, a virtual private network or some other type of network, such as dedicated access lines, plain ordinary telephone lines, satellite links, a public switched telephone network (PSTN), etc., or any suitable combination thereof. In aspects in which network 130 facilitates a connection to the Internet, data communications may take place over the network 130 via one or more suitable Internet communication protocols. Back-end components 104 may include a server 140. Server 140 may include one or more computer processors configured to execute various software applications, components of the driver's education evaluation system 100, and/or other suitable software applications.

Server 140 may further include a database 146. Database 146 may be configured to store data related to the operation of driver's education evaluation system 100. Such data might include, for example, data collected by device 110, device 111, and/or on-board computer 114, which may pertain to the driver's education evaluation system 100 and may be uploaded to the server 140 in the form of images, sensor input data, data analyzed according to the methods discussed below, or any other suitable type of data. Server 140 may access data stored in database 146 when executing various functions and tasks associated with the operation of driver's education evaluation system 100.

Although driver's education evaluation system 100 is shown in FIG. 1 as including one server 140, one device 110, one device 111, and one on-board computer 114, various aspects include driver's education evaluation system 100 implementing any suitable number of servers 140, devices 110, devices 111, and/or on-board computers 114. For example, the driver's education evaluation system 100 may include a plurality of servers 140 and a large number (e.g., 100) of devices 110, any suitable number of which may be interconnected via the network 130. Device 110 and/or device 111 may perform the various functions described herein in conjunction with on-board computer 114 or alone (in such cases, on-board computer 114 need not be present).

Furthermore, in aspects whereby more than one server 140 is implemented, processing performed by the one or more servers may be distributed among the plurality of servers in an arrangement known as "cloud computing." According to this example, this configuration may provide several advantages, such as, for example, enabling near real-time uploads and downloads of information as well as periodic uploads and downloads of information. This may provide for a thin-client aspect of device 110, device 111, and/or on-board computer 114 discussed herein as well as acting as a backup of some or all of the data gathered by device 110, device 111, and/or on-board computer 114.

Alternatively, driver's education evaluation system 100 may include only the front-end components 102. For example, device 110, device 111, and/or on-board computer 114 may perform any suitable portion of the processing associated with gathering data, receiving user input, generating driving session and/or performance reports for the student driver 106, storing the driving session and/or performance reports, and/or sending the driving session and/or performance reports to back-end components 104. As such, driver's education evaluation system 100 may be a "stand-alone" system, neither sending nor receiving information over network 130.

Server 140 may have a controller 155 that is configured to communicate with database 146 via a link 156. As will be appreciated by those of ordinary skill in the relevant art(s), while not shown, additional databases may be linked to the controller 155 in any suitable manner. Controller 155 may include a program memory 160, a processor 162, a random-access memory (RAM) 164, and an input/output (I/O) circuit 166, any combination of which may be interconnected via an address/data bus 165. In various aspects, program memory 160 may be implemented as a non-transitory tangible computer readable memory configured to store computer-readable instructions that when executed by the processor 162 cause the server 140 to perform various acts, such as implementing various applications stored in program memory 160, such as a server application 142 and a web server 143, for example.

The instructions for server application 142 may cause server 140 to implement the methods described herein. While shown as a single block in FIG. 1, various aspects include server application 142 having any suitable number of different programs, modules, routines, and/or sub-routines that may collectively cause server 140 to run server application 142. Although only one microprocessor 162 is shown in FIG. 1, various aspects of server 140 may include multiple microprocessors 162. Similarly, aspects of the memory of controller 155 may include multiple RAMs 164 and multiple program memories 160.

Further, while the instructions for server application 142 and web server 143 are shown as being stored in program memory 160, various aspects may include the instructions being additionally or alternatively stored in database 146 and/or RAM 164. Although I/O circuit 166 is shown as a single block, various aspects may include I/O circuit 166 having any suitable number and/or types of I/O circuits. RAM(s) 164 and program memories 160 may be implemented as semiconductor memories, magnetically readable memories, and/or optically readable memories, for example. The controller 155 may also be configured to communicate over network 130 via a link 135 and the I/O circuit 166.

In an aspect, device 110 and/or device 111 may be configured with suitable hardware and/or software (e.g., one or more applications, programs, files, etc.) to receive data collected from on-board computer 114 during a driving session via link 116. Additionally or alternatively, device 110 and/or device 111 may also be configured to collect data via any number of respective integrated sensors, from server 140, and/or another suitable device not shown in FIG. 1. In various aspects, device 110 and/or device 111 may receive data from on-board computer 114 via link 116, generate data via each respective device's integrated data sensors, and/or share any combination of this data between device 110 and device 111 via link 115.

Additionally or alternatively, device 110 and/or device 111 may use any suitable combination of data received from on-board computer 114 and/or generated data via each respective device's integrated data sensors to generate one or more driving session reports, real-time status data, and/or non real-time status data, which is further discussed in detail below.

As used herein, data collected from any suitable device during a driving session from one or more of device 110, device 111, server 140, and/or on-board computer 114 and/or data generated via one or more integrated sensors of one or more of device 110, device 111 and/or on-board computer 114 is collectively referred to as "status data," or "status metrics." As further discussed below, the status data may include driver status data, vehicle status data, as well as data from other suitable sources when applicable.

In some aspects, device 111 receives data from device 110 and/or on-board computer 114, but device 111 does not generate its own data. In other aspects, device 111 may generate data in addition to data received from device 110 and/or on-board computer 114 or as an alternate to data that may otherwise be received from device 110 and/or on-board computer 114.

Status data received at device 111 from on-board computer 114 via link 116 and/or generated via one or more integrated sensors of device 110 and/or device 111 may include, for example, data corresponding to a status of driver 106 and/or a status of vehicle 108. Examples of driver status data may include data related to one or more driver actions such as driver eye movement, a direction of a driver's gaze, driver head position, one or more driver biometrics, etc. Examples of vehicle status data may include data related to a steering, acceleration, braking, road speed, engine speed, a distance between vehicle 108 and a second vehicle in front of vehicle 108, lane position of vehicle 108, vehicle light status (e.g., whether headlights are on or off), a geographic position of vehicle 108, whether a turn signal has been activated, whether windshield wipers are activated, etc.

In an aspect, once the driving session has ended, device 110 and/or device 111 may generate a driving session report to provide feedback to the student driver using the status data. In accordance with an aspect, device 110 and/or device 111 may be configured to generate one or more driving session reports and/or feedback scores based on the status data using any of the techniques as described in commonly-assigned U.S. application Ser. No. 13/844,090, which is hereby incorporated by reference in its entirety. Additionally, on-board computer 114, device 110, and/or device 111 may utilize any of the techniques described in U.S. application Ser. No. 13/844,090 to process driver status data and/or vehicle status data for the generation of driving session reports.

Further in accordance with such aspects, device 110 and/or device 111 may be configured to generate one or more tagged driving events based on the status data and/or data that is input by a user, such as a driving instructor, for example. Device 110 and/or device 111 may utilize these tagged driving events to generate the driving session report. Examples of aspects including the generation of tagged driving events and their inclusion in the driving session report may be implemented using any of the techniques as described throughout this disclosure as well as those described in commonly-assigned co-pending U.S. application Ser. No. 14/494,088, which is hereby incorporated by reference in its entirety.

In various aspects, device 111 may be configured to generate one or more status metrics based on the status data. In an aspect, device 111 may generate the status metrics as the status data is received and/or generated, i.e., in real-time. The status metrics may include, for example, one or more calculated values and/or conditions interpreted from the status data. For example, if the status data includes the vehicle's current speed, then the corresponding generated status metric may be a corresponding numeric value in terms of miles per hour (mph), kilometers per hour (kph), etc.

To provide another example, if the status data includes the driver's gaze, then the corresponding status metric could include tabular data corresponding to a gaze chart. To provide yet another example, if the status data included a driver's head position, then the corresponding status metric could include a condition associated with whether the driver checked his blind spot or not, such as "true" or "false." Gaze tracking and a gaze chart may be determined and/or calculated by implementing any suitable technique, such as those described in commonly-assigned co-pending U.S. application Ser. No. 14/282,437, filed on May 20, 2014, which is hereby incorporated by reference in its entirety.

In some aspects, device 111 may be configured to format and/or display the generated status metrics in real-time such that the status metrics are indicative of a current status of driver 106 and/or vehicle 108. For example, device 111 may be configured to display the vehicle's current speed.

In other aspects, device 111 may be configured to format and/or display any suitable portion of the generated status metrics as real-time metrics and/or non real-time metrics. For example, device 111 may be configured to display some (or all) status metrics indicative of a real-time status of driver 106 and/or vehicle 108 while displaying other status metrics (or all status metrics) that are not indicative of a real-time status of driver 106 and/or vehicle 108. For example, device 111 may be configured to display non-real time status metrics such as averaged and/or aggregated status metrics at the end of a driving session, for example.

Device 111 may also be configured to display both real-time metrics and non real-time metrics at the same time. For example, device 111 may display a real-time status metric indicative of the current speed of vehicle 108 while also displaying a non real-time driver feedback score retrieved from a student's previous driving session. The driver feedback score may be calculated and/or retrieved, for example, according to any suitable techniques as described in U.S. application Ser. No. 13/844,090. In this way, driver's education evaluation system 100 provides feedback regarding a current and/or previous status of a driver and/or vehicle during and after a driving session.

II. Operation of Device 110, Device 111, and/or on-Board Computer 114

Figure 2:
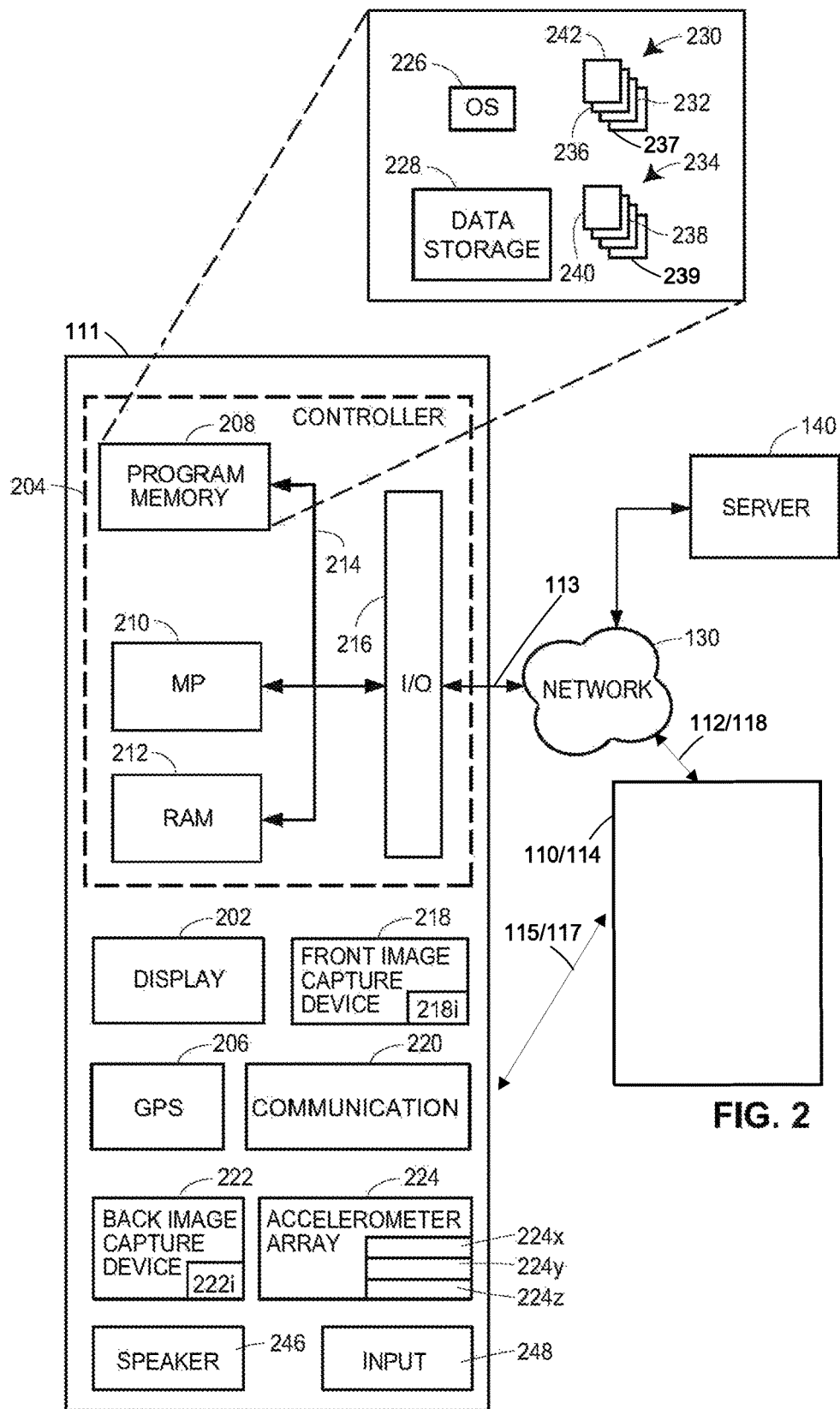
FIG. 2 illustrates a detailed block diagram of a portion of exemplary driver's education evaluation system 100 in accordance with an exemplary aspect of the present disclosure.

FIG. 2 illustrates a detailed block diagram of a portion of exemplary driver's education evaluation system 100 in accordance with an exemplary aspect of the present disclosure. Device 110 and/or on-board computer 114 may share several of the same components as device 111 to facilitate similar functions, as shown in FIG. 2. As a result, the individual components of device 110 and on-board computer 114 are not shown in FIG. 2 for purposes of brevity, and only differences between device 110, device 111, and on-board computer 114 will be further discussed herein.

Device 111 may include a display 202, a Global Positioning System (GPS) unit 206, a communication unit 220, a front image capture device 218, a back image capture device 222, an accelerometer array 224, a user-input device 248, a speaker 246, and a controller 204.

Controller 204 includes a program memory 208, one or more of a microcontroller or a microprocessor (MP) 210, a random-access memory (RAM) 212, and an input/output (I/O) circuit 216, each of which is interconnected via an address/data bus 214. In various aspects, program memory 208 may be implemented as a non-transitory tangible computer readable media configured to store computer-readable instructions that when executed by controller 204 cause controller 204 to perform various acts. In various aspects, program memory 208 may include various portions that may include instructions associated with corresponding functions to be performed by controller 204. For example, as shown in FIG. 2, program memory 208 may include an operating system 226, a plurality of software applications 230, and/or a plurality of software routines 234. To provide another example, program memory 208 may include other portions to store data that may be read from and written to by processor 210, such as data storage 228, for example.

In an aspect, operating system 226 may be implemented as any suitable operating system platform depending on the particular implementation of device 110, device 111, and/or on-board computer 114. For example, operating system 226 may be implemented as one of a plurality of mobile platforms such as the iOS®, Android™, Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively.

In an aspect, data storage 228 may include data such as user profiles and preferences, application data for the plurality of applications 230, routine data for the plurality of routines 234, any suitable data necessary to interact with the server 140 via network 130, and any suitable data necessary to interact with the device 110 and/or onboard computer 114. In some aspects, controller 204 may also be configured to communicate with additional data storage mechanisms (e.g., one or more hard disk drives, optical storage drives, solid state storage devices, etc.) that reside within device 111.

In an aspect, GPS unit 206 may use "Assisted GPS" (A-GPS), satellite GPS, or any other suitable global positioning protocol (e.g., the GLONASS system operated by the Russian government) or system that locates the position device 111. For example, A-GPS may utilize cell phone towers or Wi-Fi hotspots (e.g., wireless router points) via communications sent and/or received via communication unit 220 to more accurately and more quickly determine location of device 111. On the other hand, satellite GPS is typically more useful in more remote regions that lack cell towers or Wi-Fi hotspots.

In an aspect, front and back image capture devices 218 and 222 may be integrated as part of device 110 and/or device 111 and may be implemented as peripheral cameras, such as webcams, cameras installed inside the vehicle 108, cameras installed outside the vehicle 108, etc., that are configured to communicate with suitable portions of device 110 and/or device 111.

In an aspect, front image capture device 218 and/or back image capture device 222 may be integrated as part of device 110. In accordance with such embodiments, status data may be sent to device 111 from device 110 using information derived from front image capture device 218 and/or back image capture device 222. For example, device 110 may include front image capture device 218 oriented toward student driver 106 to observe student driver 106 as part of one or more autonomous data collection processes, such as eye tracking, for example. To provide another example, device 110 may include back image capture device 222 oriented toward the front of vehicle 108 to observe the road, lane markings, and/or other objects in front of vehicle 108 as part of one or more autonomous data collection processes, such as determining a following distance, for example.

In some aspects, data may be collected from both front image capture device 218 and back image capture device 222 simultaneously. In other aspects, data may be collected from front image capture device 218 and back image capture device 222 at separate time intervals, such as in accordance with a time-division multiplexing schedule, for example.

In some aspects, device 110 and/or device 111 may include both a front image capture device 218 and a back image capture device 222. In other aspects, device 110 and/or device 111 may include only front image capture device 218 or back image capture device 222. Front image capture device 218 and/or back image capture device 222 may include an infrared illuminator 218$i$, 222$i$, respectively, to facilitate low light and/or night image capturing. Infrared illuminator 218$i$, 222$i$ may be activated when light is insufficient for image capturing.

In an aspect, accelerometer array 224 may be implemented as one or more accelerometers positioned to determine the force and direction of movements of device 110 and/or device 111. In some aspects, accelerometer array 224 may include an X-axis accelerometer 224$x$, a Y-axis accelerometer 224$y$, and a Z-axis accelerometer 224$z$ configured to measure the force and direction of movement in each dimension, respectively. As will be appreciated by those of ordinary skill in the relevant art(s), a three dimensional vector describing movement of device 110 and/or device 111 through three dimensional space can be established by combining the outputs of the X-axis, Y-axis, and Z-axis accelerometers 224$x$, $y$, and $z$ using any suitable methods.

GPS unit 206, front image capture device 218, back image capture device 222, and accelerometer array 224 may be referred to collectively as the "sensors" of device 110 and/or device 111. As will be appreciated by those of ordinary skill in the relevant art(s), various aspects of device 110 and/or device 111 include any suitable number of additional GPS units 206, front image capture devices 218, back image capture devices 222, and/or accelerometer arrays 224.

Communication unit 220 may communicate with server 140 using any suitable communication protocol over network 130 via link 113. Additionally or alternatively, communication unit 220 may communicate with device 110 and/or on-board computer 114 using any suitable communication protocol via links 115 and 117, respectively. Examples of communications protocols include wireless telephony network (e.g., GSM, CDMA, LTE, etc.) protocols, Wi-Fi network (802.11 standards) protocols, WiMAX network protocols, BLUETOOTH network protocols, etc. Communication unit 220 may also be capable of communicating using a near field communication standard (e.g., ISO/IEC 18092, standards provided by the NFC Forum, etc.). Further, communication unit 220 may use one or more wired connections to facilitate communications with server 140, device 110, and/or on-board computer 114.

In various aspects, user-input device 248 may be implemented as any suitable device configured to collect user input, such as a "soft" keyboard that is displayed on the display 202 of device 110 and/or on-board computer 114, an external hardware keyboard communicating via a wired or a wireless connection (e.g., a Bluetooth keyboard), an external mouse, etc. User-input device 248 may also include a microphone configured to receive user voice input. As previously discussed with reference to controllers 155 and 224, as will be appreciated by those of ordinary skill in the relevant art(s), although FIG. 2 depicts only one processor 210, controller 204 may include any suitable number of MPs 210.

Memory of controller 204 may include any suitable number of RAMs 212 and any suitable number of program memories 208. Although FIG. 2 depicts I/O circuit 216 as a single block, various aspects of I/O circuit 216 may include any suitable number of different types of I/O circuits. In various aspects, controller 204 may implement RAM(s) 212 and program memories 208 as any suitable type of memory, such as non-transitory computer readable memories, semiconductor memories, magnetically readable memories, and/or optically readable memories, for example.

In various aspects, one or more processors 210 may be configured to execute any of one or more of the plurality of software applications 230 and/or any one or more of the plurality of software routines 234 residing in program memory 208 in addition to other software applications.

In an aspect, one of the plurality of applications 230 may be a client application 232 that may be implemented as a series of machine-readable instructions for performing the various tasks associated with implementing the driver's education evaluation system 100 as well as receiving information, displaying information, and/or transmitting information between device 110, device 111, on-board computer 114, and/or server 140.

In various aspects, any of the plurality of applications 230 may be implemented as a stand-alone system or as a system wherein the front-end components 102 communicate with back-end components 104 as described herein. Additionally, any of the plurality of applications 230 may include machine-readable instruction for implementing a user interface to allow a user to input commands to and receive information from driver's education evaluation system 100 in accordance with the functionality supported by each respective application.

One of the plurality of applications 230 may be a native web browser 236, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server 140 or other back-end components 104 while also receiving inputs from the user. Another one of the plurality of applications 230 may include an embedded web browser 242 that may be implemented as a series of machine-readable instructions for receiving, interpreting, and displaying web page information from the servers 140 or other back-end components 104 within client application 232.

Additionally, server 140 may include any suitable number of software applications. In various aspects, server 140 may include software applications configured to facilitate the generation of data content to be included in the web pages sent from the web server 143 to the device 110, device 111, and/or on-board computer 114. The software applications may be executed on the same computer processor as web server application 143, or on different computer processors.

In aspects in which device 110, device 111, and/or on-board computer 114 is a thin-client device, server 140 may perform any suitable portion of the processing functions remotely that would otherwise be performed by device 110, device 111, and/or on-board computer 114. In such aspects, device 110, device 111, and/or on-board computer 114 may gather data from its respective sensors as described herein, but device 110, device 111, and/or on-board computer 114 may send the data to server 140 for remote processing instead of analyzing the data locally. In such aspects, server 140 may perform the analysis of the gathered data, which may include any combination of status data and/or driving events collected via sensors and/or input by a user to generate a feedback score, status metrics, a driving session report, etc.

As previously discussed, various aspects of driver's education evaluation system 100 may be performed by any combination of device 110, device 111, on-board computer 114, and/or server 140. In aspects in which device 110, device 111, and/or on-board computer 114 offload processing tasks to server 140, native web browser 236 and/or embedded web browser 242 may facilitate the transfer of data using one or more web-based applications.

One of the plurality of routines 234 may include an image capture routine 238 that coordinates with the image capture devices 218, 222 to retrieve image data for use with one or more of the plurality of applications, such as the client application 232, or for use with any other suitable routines. Another routine in the plurality of routines may include an accelerometer routine 240 that determines the force and direction of movements of device 110 and/or device 111. The accelerometer routine 240 may process data from the accelerometer array 224 to determine a vector describing the motion of device 110 and/or device 111 for use with the client application 232. In some aspects where the accelerometer array 224 has X-axis, Y-axis, and Z-axis accelerometers 224x, y, z, the accelerometer routine 240 may combine the data from each accelerometer 224x, y, and z to establish a vector describing the motion of device 110 and/or device 111 through three dimensional space. Furthermore, in some aspects, the accelerometer routine 240 may use data pertaining to less than three axes, such as when determining when vehicle 108 is braking.

One of the plurality of applications 230 may include a feedback application 237. In an aspect, feedback application 237 may be an application that is installed on device 111. For example, feedback application 237 may be downloaded and installed to device 111 by a user. In an aspect, feedback application 237 may include instructions for implementing a user interface to allow a user to input commands and/or respond to prompts. For example, feedback application 237 may allow a user to select one or more options associated with displaying status metrics, feedback scores, saving driving session reports, saving status metrics, generating driving session reports, etc.

Additionally or alternatively, feedback application 237 may include instructions for receiving data input from a user (e.g., via input 248), sending data to and receiving data from server 140 (e.g., via I/O 216), sending data to and receiving data from device 110, and/or on-board computer 114 (e.g., via communication unit 220), and/or generating data associated with one or more sensors integrated within device 111 (e.g., GPS unit 206, accelerometer array 224, etc.). For example, feedback application 237 may receive data from GPS unit 206 to determine a geographic location of vehicle 108 throughout the driving session, and use this data to facilitate displaying the position of vehicle 108 on a map in real-time.

In an aspect, one of the plurality of routines 234 may include a feedback generation and display routine 239. As used herein, "feedback data" may include any portion of data received, processed, generated, calculated, displayed, etc., on a display of a respective device during a driving session. For example, feedback generation and display routine 239 may process data collected via any suitable number of the plurality of applications 230 and/or the plurality of routines 234 to generate feedback data such as one or more status metrics, a feedback score, driving session reports, etc.

As will be appreciated by those of ordinary skill in the relevant art(s), any suitable routine may be implemented by feedback generation and display routine 239 to generate and display the feedback data. In various aspects, feedback generation and display routine 239 may process data received and/or generated via feedback application 237 to generate the feedback data and/or format the feedback data for display on display 202. The feedback data may be displayed via display 202, sent to server 140 via network 130, and/or sent to another suitable device via communication unit 220, such as device 110, for example.

Feedback generation and display routine 239 and/or feedback application 237 may facilitate any suitable portion of the feedback data being sent to another device and/or stored on another device in any suitable format that may be accessed and viewed by a user. For example, the feedback data may be saved to device 111, emailed to device 110 or another device, stored on server 140 or another online storage medium, etc.

In an aspect, feedback generation and display routine 239 may process data received and/or generated by feedback application 237 to determine a current time and/or a time associated with various portions of data received and/or generated by feedback application 237. For example, feedback generation and display routine 239 may derive a network time from data received from server 140. To provide another example, feedback generation and display routine 239 may determine a time associated with status data received and/or generated by feedback application 237 that may correspond to a driving event, such as a time corresponding to a lane change, a braking event, etc. In some aspects, feedback generation and display routine 239 may determine a current time from a time that is associated with the respective received or generated data through the use of a real-time clock, which may be integrated as part of controller 204, for example. A real-time clock is not shown in FIG. 2 for purposes of brevity.

In other aspects, feedback generation and display routine 239 may determine a time associated with status data received by feedback application 237 if the received status data includes a timestamp or other suitable time identifier from which to derive the time of the event. For example, as will be appreciated by those of ordinary skill in the relevant art(s), on-board computer 114 may be configured to timestamp status data as it is processed, and to send this data to device 111 with the timestamp information. Once the time is determined by feedback generation and display routine 239, device 111 may keep track of not only generated and/or status data received from device 110 and/or on-board computer 114, but when the received status data was initially generated.

Feedback generation and display routine 239 may utilize the time associated with various types of status data to generate updated status metrics, an updated driver feedback score, an updated time until the driving session will end, etc. For example, feedback generation and display routine 239 may calculate a moving average of a driver feedback score throughout a driving session over a period of time using a timestamp associated with each driving event, for example.

In various aspects, the driving session report may include varying details of the feedback data to provide the driver with feedback regarding her driving performance skills. For example, the driving session report may include a driver feedback score, any driving events that were recorded by respective sensors, input entered by an instructor, a mapped route of the driving session, one or more tagged driving events (as further discussed below), one or more status metrics collected during the driving session, etc.

Additionally or alternatively, any suitable number of tagged driving events may be generated by feedback generation and display routine 239 using the data received and/or generated via feedback application 237. In accordance with such an example, the driving session report could be generated using any suitable techniques as described in the commonly assigned U.S. application Ser. No. 13/844,090.

Feedback data displayed to a user may include both positive and negative types of information. For example, an instructor could enter information that a turn was particularly well executed, that a student performed a slow and steady stop without excessive jerking, etc. Although most driving tests do not utilize positive types of driving event feedback for scoring purposes, this type of information is still valuable to student drivers who are still learning their strengths and weaknesses throughout the evaluation process.

Although FIG. 2 shows details of device 111 and describes functions of device 111 in terms of various elements of device 111, various aspects include device 110 and/or onboard computer 114 collecting status data and sending any suitable type and amount of data to device 111. Further in accordance with such aspects, device 111 may receive status data and any other suitable data from device 110, server 140, and/or on-board computer 114 without device 111 generating any status data. In such a case, device 111 may generate one or more status metrics, driver feedback scores, etc., based on status data and/or other suitable data received from one or more of device 110, server 140, and/or on-board computer 114. As will be appreciated by those of ordinary skill in the relevant art(s), device 111 may be implemented having less elements than shown in FIG. 2 to accomplish such functions.

III. Example Process of Saving and Recalling Driver Profiles

In various aspects, feedback application 237 may be configured to facilitate the creation of driver profiles. Once created and saved after a driving session has been completed, driver profiles may include an aggregation of driving data such as previous feedback scores, a history of status data collected during previous driving sessions, previous driving session reports, etc.

In accordance with various aspects, a user may utilize a suitable device, such as device 111, for example, as shown FIG. 1, to enter details about one or more drivers to create a driver profile. In an aspect, a user may utilize user-input device 248 to enter this information. The details entered to create the driver profile may include, for example, the driver's name, contact information, email address, guardian contact information, etc. In various aspects, a user may specify additional information to be associated with the driver profile such as a driving group, for example. The designation of a driving group may be particularly useful when the driver profile is for one student from among several students that are taught as part of a class or a group of classes, for example.

In various aspects, a user may choose to store one or more driver profiles locally to the device used to create the driver profile or to another device. For example, if an instructor created one or more driver profiles on device 111, then the instructor could choose to save the driver profiles on device 111, device 110, or database 146.

In various aspects, prior to starting a driving session, a user may select the appropriate driver profile using device 111. For example, a driver profile corresponding to "John Smith" may be stored in a suitable portion of memory associated with device 111, such as data storage 228, for example, and be retrieved by controller 204 upon selection of the respective driver profile by a user prior to the start of a new driving session. To provide another example, device 111 may download the driver profile corresponding to "John Smith" from server 140 using a suitable communications link, such as links 113 and/or 115, for example, upon selection of the respective driver profile by a user prior to the start of a new driving session.

In various aspects, application 237 may facilitate the selection of a driver profile by a user that is organized in a suitable way, such as alphabetically, for example. To provide another example, application 237 may facilitate a user locating the driver profile from several driver profiles having the same corresponding group designation.

As will be appreciated by those of ordinary skill in the relevant art(s), various aspects include the creation, storage, identification, and retrieval of driver profiles using any suitable method, such as any suitable techniques as described in commonly-assigned co-pending U.S. patent application Ser. No. 14/699,758, which is hereby incorporated by reference in its entirety.

IV. Example Screenshot of a Current Driving Session Feedback Data Display

Figure 3:
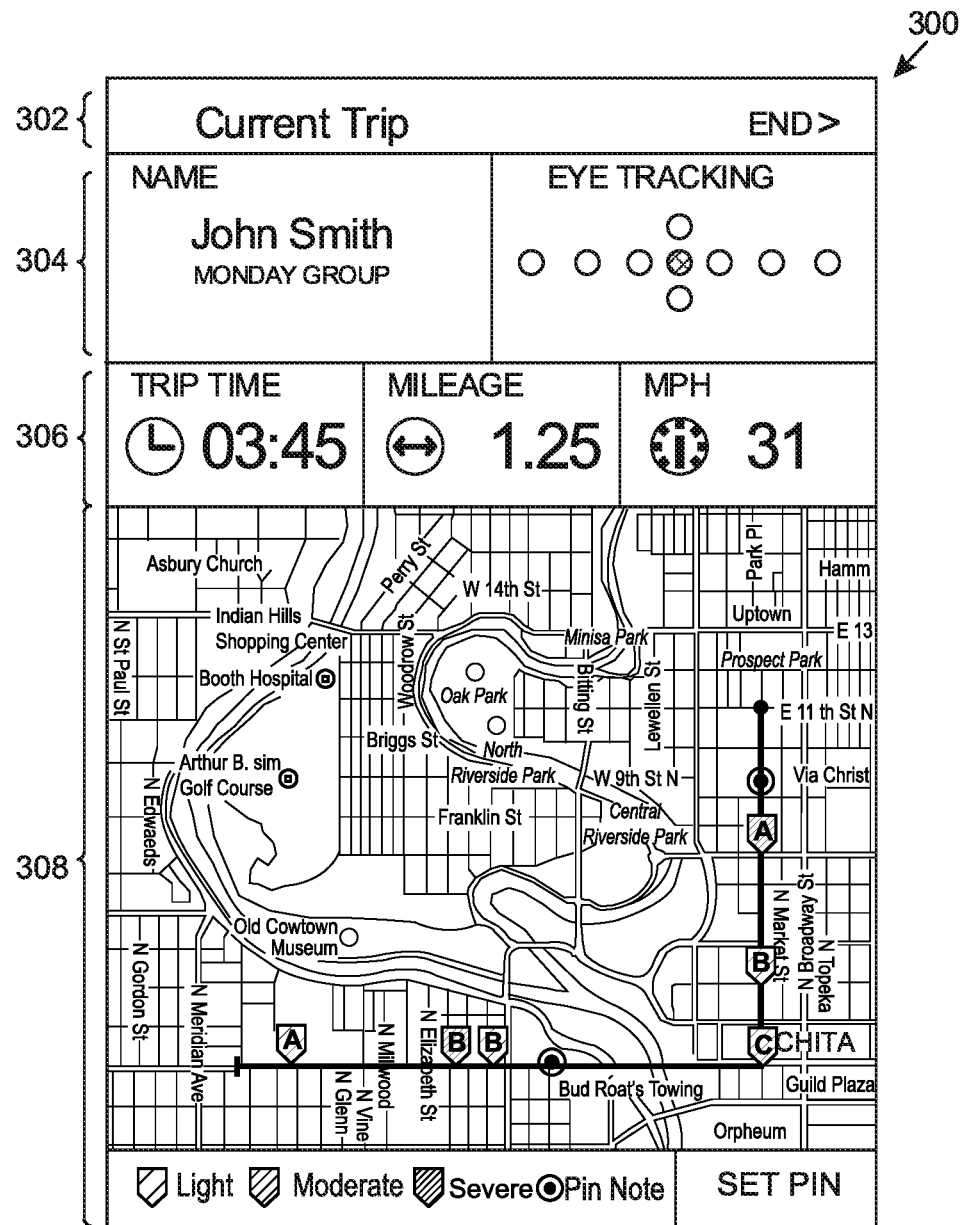
FIG. 3 illustrates an example screenshot 300 of a device used to display current driving feedback data during a driving session in accordance with an exemplary aspect of the present disclosure.

FIG. 3 illustrates an example screenshot 300 of a device used to display current driving feedback data during a driving session in accordance with an exemplary aspect of the present disclosure. Feedback data may include, for example, the data shown in any of the portions of screenshot 300, which is further discussed below.

Screenshot 300 may include portions 302, 304, 306, and 308. In the present aspects, the following screenshot shown in FIG. 3 is an example of what may be displayed to a user as part of a driver feedback application. In the present aspects, screenshot 300 may be displayed using any suitable interface device, such as display 202, for example, as shown in FIG. 2. As will be appreciated by those of ordinary skill in the relevant art(s), the example screenshot 300 shown in FIG. 3 is for illustrative purposes, and any suitable relevant data as discussed throughout this disclosure, such as status metrics, for example, may be displayed to a user using any suitable format and/or design without departing from the spirit and scope of the present disclosure.

Portion 302 may include any suitable graphic, information, label, etc., to indicate a status of the driving session, which may be a label such as "current trip" as shown in FIG. 3, or a custom name entered by a user prior to the driving session. For example, a user may choose to name the driving session any suitable name to later correlate the driving session report with the appropriate student, group, instructor, etc. In some aspects, portion 302 may be implemented as an interactive portion of a respective display. For example, an instructor may select the "end" label of portion 302 to end a current driving session and store the details of the driving session as part of the corresponding driver profile for the driver John Smith, which will be further discussed in detail below.

Portion 304 may include any suitable graphic, information, label, etc., to indicate a driver's name and/or group, which may be the current driver of the vehicle, for example. In an aspect, the driver's name and/or associated designation (e.g., "Monday Group") displayed in portion 304 may be part of a driver profile that is selected by a user from a set of driver profiles before the driving session is started, as previously discussed.

Portion 304 may include any suitable graphic, information, label, etc., to indicate an eye tracking gaze chart. As previously discussed, any suitable methods may be utilized to calculate the driver's gaze, or direction of eye movement, during the driving session. In an aspect, this gaze chart may be displayed in portion 304 in real-time. In this way, aspects of feedback application 237 provide a driving instructor a way to view details of a student driver and to monitor the student's eye movement in real time during a driving session.

Portion 306 may include any suitable graphic, information, label, etc., to indicate any suitable number of status metrics based on status data corresponding to a status of driver 106, and/or a status of vehicle 108. As previously discussed with reference to FIGS. 1 and 2, aspects include the status metrics being obtained from the status data in conjunction with any suitable number of relevant sensors.

As shown in FIG. 3, portion 306 includes status metrics such as the current driving session trip time, the current driving session mileage accrued since the start of the driving session, and the current vehicle speed. Although only three status metrics are shown in portion 306, portion 306 (or another suitable portion of screenshot 300) may include any suitable number of suitable graphics, information, labels, etc., indicative of any suitable number of status metrics. For example, in addition to the status metrics shown in FIG. 3, screenshot 300 may display information representative of a following distance between the vehicle and another vehicle in front of the vehicle ("time to collision," or "TTC"), a lane position of the vehicle, a braking status (e.g., "braking"), a driver biometric status indication (e.g., "anxious"), current weather conditions, etc.

Portion 308 may include any suitable graphic, information, label, etc., to indicate one or more tagged driving events superimposed over a map of a route corresponding to a current driving session. Although not shown in FIG. 3, the map displayed in portion 308 may include an indication of the start of the route, the end of the route, and/or a current position and/or direction of the vehicle. In various aspects, tagged driving events may be generated based on a comparison between one or more status metrics and one or more predetermined threshold values and/or conditions being met or not being met. These tagged driving events may correspond to various safety and/or driving performance considerations, such as acceleration, braking, and cornering, for example. As shown in portion 308, acceleration, braking, and cornering tagged driving events correspond to the labels "A," "B," and "C," respectively. Since the location of the vehicle is monitored concurrently with the status metric data, each of the tagged driving events may be placed on the map at the respective location where each event occurred.

Although only acceleration, cornering, and braking driving events are shown in portion 308, various embodiments include any suitable number of tagged driving events being generated and/or displayed on the map in portion 308. For example, if the current status metrics indicate that the current vehicle speed is 31 mph and the posted speed limit is 20 mph, then portion 308 may indicate this as a tagged driving event with an appropriate label, such as "S," for example. In various aspects, the tagged driving events may be generated when a current relevant status metric is greater than or less than a predetermined threshold value. Using the acceleration of the vehicle as an example, a tagged driving event may be generated when the measured acceleration determined from the respective status metrics exceeds 1.5 $m/s^2$. To provide another example, a tagged driving event may be created when the vehicle speed is equal to or greater than 5 mph over the posted speed limit.

In various aspects, a scale may be used to compare the status metrics for each respective driving event to a range of thresholds, and to label the status metrics with a severity level accordingly. For example, as shown in FIG. 3, portion 308 may include a color-coded or other suitable type of labeling system to indicate more excessive acceleration, cornering, braking, etc. As will be appreciated by those of ordinary skill in the relevant art(s), these severity scales may be based on any suitable range of threshold values for each type of tagged driving event. Using acceleration as an example, a base threshold may be set as 1.4 $m/s^2$. Once a driver accelerates beyond this threshold, a "light" severity tagged driving event may be generated and placed on the map in portion 308. A moderate acceleration tagged driving event could correspond to acceleration values less than 2.4 $m/s^2$ but greater than 2.0 $m/s^2$, for example, while severe acceleration tagged driving events could correspond to those exceeding 2.4 $m/s^2$, for example. As will be appreciated by those of ordinary skill in the relevant art(s), status metric data may be measured in accordance with any suitable relevant sensor to calculate the desired corresponding status metric.

In various aspects, the thresholds, or threshold ranges, used to determine the severity of tagged driving events may be determined based on a number of conditions. For example, thresholds (or threshold ranges) may change dynamically based on changes in the status metrics. For example, a tagged driving event may be generated when a driver is following another vehicle closer than a threshold distance, but an acceptable threshold distance may be dependent on the vehicle's speed and/or other factors, such as the weather conditions. Aspects include tagged driving event thresholds being adjusted from an initial threshold value, such as distance between cars, for example, based on these factors.

To provide another example, threshold ranges may be associated with a type of vehicle, which could be part of the driver's profile. For example, if a driver has an assigned car, then these threshold ranges may be used to generate tagged driving events using vehicle-specific thresholds based on the type of car used by the driver. For example, a sport utility vehicle (SUV) may be assigned lower tagged driving event severity thresholds for cornering events than a those for a sedan.

In various aspects, threshold ranges or other conditions triggering the generation of a tagged driving event may be based on any suitable portion of the supplemental data. For example, as will be appreciated by those of ordinary skill in the relevant art(s), a TTC value may be determined from a calculated time-to-stop based on a current vehicle speed and distance between vehicles. Therefore, a threshold TTC may be decreased if the supplemental data includes weather information indicating that it is raining.

To provide another example, a threshold speed limit may be reduced from 5 miles over the posted limit to 5 miles under the posted limit in rainy conditions. To provide yet another example, a tagged driving event may be generated only when the supplemental data warrants such a condition. To illustrate this example, if the vehicle lights are off when it is raining during the daytime an tagged driving event may be generated if this is a requirement in accordance with state and/or local laws, even though a tagged driving event would not otherwise be generated during the daytime. In this way, a relevant application and/or routine, such as feedback application 237 and/or feedback generation and display routine 239, for example, may dynamically interpret new status data and/or supplemental data to continuously adjust the appropriate thresholds associated with the generation of tagged driving events in real-time.

In various aspects, data that is compared to the status metrics to generate the tagged driving events may be received, calculated, and/or generated from another suitable device. For example, as will be appreciated by those of ordinary skill in the relevant art(s), GPS data may be referenced to determine the posted speed limit corresponding to the vehicle's current location. Application 237 and/or display routine 239 may use this posted speed limit data to generate tagged driving events based on a comparison between the vehicle's current speed and the posted speed limit data derived from the status and/or supplemental data.

Additionally or alternatively, portion 308 may include an interactive portion, such as the "SET PIN" portion shown in FIG. 3, for example. In accordance with such aspects, a user may use this interactive portion to manually generate any suitable number of custom tagged driving events. For example, two custom tagged driving events are shown in FIG. 3 as part of portion 308, which are indicated by the "pin note" legend icon shown in portion 308. These custom tagged driving events may be entered by an instructor as they are observed, thus placing each custom tagged driving event on the map within portion 308 at the location of the vehicle where each event occurred. In addition to the entry of the custom tagged driving event on the map, a user may also enter a note and/or description associated with the driving event. For example, a driving instructor could enter a description such as "no complete stop at intersection of Elm and Main," "driver did not come to a complete stop," etc. Custom tagged driving events may be particularly useful when a driving instructor observes an event that is important to access a student's driving skills but may not be indicated (or easily determined from) the status metrics.

In various aspects, a pull down menu may be utilized by a user to enter text for a corresponding driving event. In various aspects, a note entered by a user may be stored and later accessed via a pull-down menu, as shown by the symbol next to the text entry in FIG. 3. In this way, commonly used notes may be quickly accessed and reused for subsequent driving events throughout a driving session. In some aspects, common text entries may be stored in the pull down menu for quick access throughout the driving session. These "quick" entries may be preloaded with feedback application 237, for example.

In addition, various aspects include portion 308 displaying any suitable number of tagged driving events, such as those described in commonly-assigned co-pending U.S. application Ser. No. 14/494,088, as previously discussed.

In some aspects, once the driving session has ended, a user may select "end" from within portion 302 to indicate the end of the driving session. For example, a user may tap his finger on this part of portion 302 with his finger. Upon the user selecting the "end" function, any suitable portion of the feedback data may be sent to another device, saved locally or stored to another device. As previously discussed with respect to FIG. 1, for example, the portion indicating "end" may allow a user to generate and/or to save driving session reports and/or any feedback data such as the status metrics, tagged driving events generated during the driving session, the mapped route of the driving session, etc., to a device, which may be the same device or a different device as the device in which screenshot 300 is displayed.

The user may choose to end the driving session at the actual end of the driving session or prematurely. If the user ends the driving session prematurely, any feedback data saved or shared, and/or any driving session report generated after the driving session has prematurely ended may be based on the feedback data collected up to the point when the driving session was ended.

In other aspects, the end of the driving session may be determined without user intervention. This determination could be made, for example, based on a comparison of an elapsed time and/or a position of the vehicle within a predetermined driving session route, for example. In accordance with such aspects, this determination may be made through utilization of the appropriate status metrics, such as GPS data, for example.

In aspects whereby the end of the driving session is determined without user intervention, one or more actions may be executed upon such a determination. For example, if GPS data indicates that the driving session has ended, a driving session report may be automatically generated and sent to another device. To provide another example, if the GPS data indicates that the driving session has ended, the feedback data collected during the driving session may be automatically saved to a suitable device, emailed to a user, etc.

V. Example Screenshot of a Driving Session Report Display

Figure 4A:
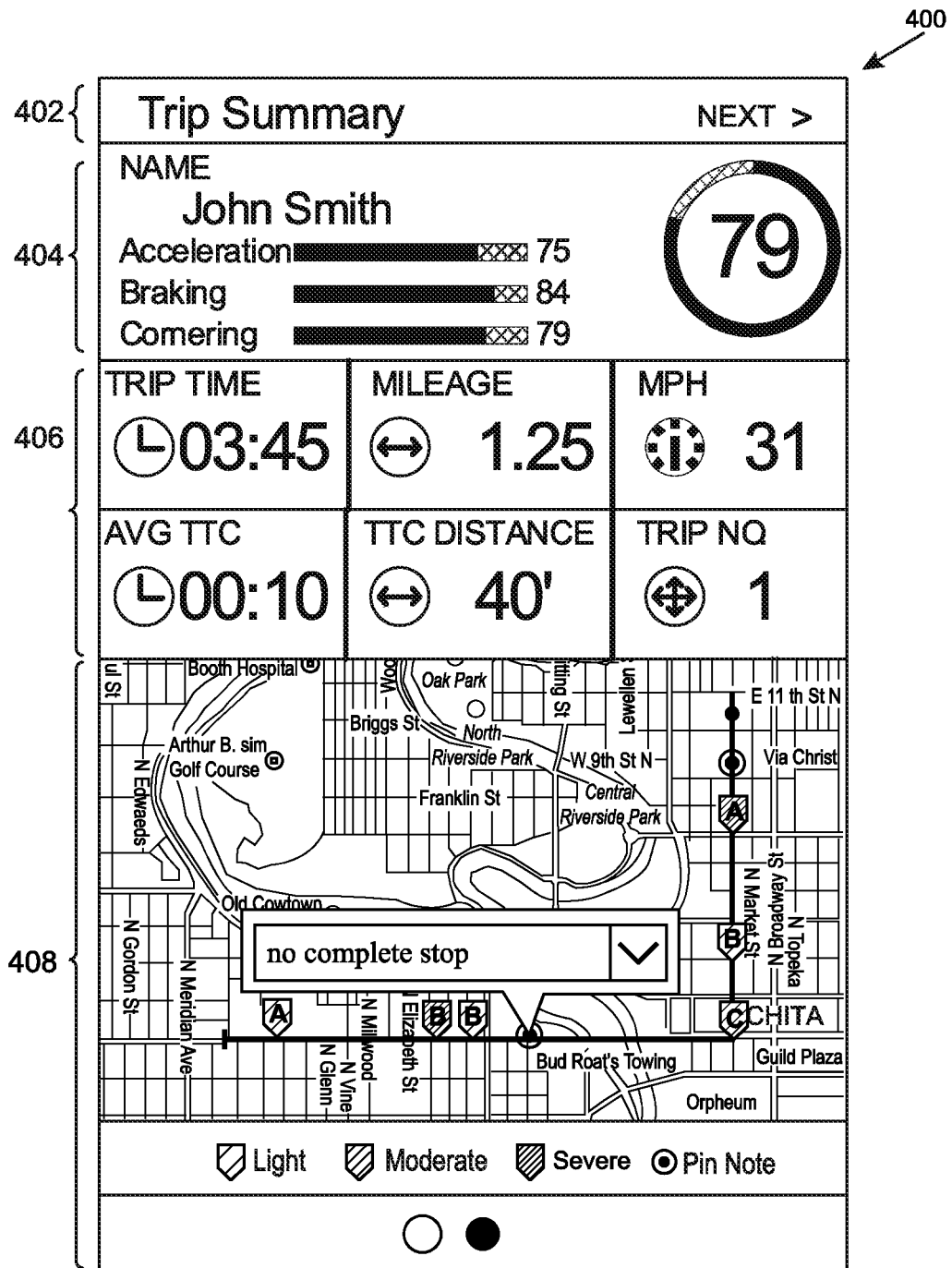
FIG. 4A illustrates an example screenshot 400 of a device used to display a driving session report after a driving session has been completed in accordance with an exemplary aspect of the present disclosure.

FIG. 4A illustrates an example screenshot 400 of a device used to display a driving session report after a driving session has been completed in accordance with an exemplary aspect of the present disclosure. In the present aspects, screenshot 400 is an example of what may be displayed to a user as part of a driving session report. In an aspect, screenshot 400 may be displayed to a user upon a user selecting, or feedback application 237 detecting, the end of a driving session, as previously discussed with reference to FIG. 3.

In the present aspects, screenshot 400 may be displayed using any suitable interface device, such as display 202, for example, as shown in FIG. 2. As will be appreciated by those of ordinary skill in the relevant art(s), the example screenshot 400 shown in FIG. 4 is for illustrative purposes, and any suitable data as described herein may be included as part of the driving session report and be displayed to a user using any suitable format and/or design without departing from the spirit and scope of the present disclosure.

Portion 402 may include any suitable graphic, information, label, etc., to indicate that the user is viewing the driving session report, which may be a label such as "trip summary," for example, as shown in FIG. 4.

Portion 404 may include any suitable graphic, information, label, etc., to indicate the driver's name, any suitable feedback data measured for a selected driving session, such as status metrics, for example, and/or a feedback score, rating, or other suitable assessment indicative of the driver's skills based on a selected driving session. Using the example of the driving session discussed with reference to FIG. 3, screenshot 400 may be an example of a driving session report that is displayed once the driver has completed the driving session route as shown in portion 308 of FIG. 3, as previously discussed. To provide another example, the driving session report shown in FIG. 4A may be loaded onto a suitable device upon selection of a corresponding driver profile, for example, in this case a driver profile of John Smith.

As shown in FIG. 4A, portion 404 may include the driver's current feedback score calculated from feedback data measured during a corresponding driving session, which may be represented graphically and/or numerically. The example shown in FIG. 4A includes both a numeric ("79") and graphical (circular icon) representation of the driver feedback score. In the example shown in FIG. 4A, the driver's feedback score is evaluated using an average of three status metric values corresponding to acceleration, braking, and cornering. Although a straight average formula is used to determine a driver feedback score of 79 in FIG. 4A, aspects include using a weighted average to assign greater weights to some status metrics over others, such as weighting acceleration twice as heavily as braking and cornering, etc. Although only three status metric values are shown in FIG. 4A, aspects include any suitable number of status metrics being displayed as part of the driving session report. Aspects include the driver feedback score being based on any suitable combination of status metrics, whether or not these status metrics are displayed in screenshot 400.

In various aspects, the status metric values may be calculated using any suitable numeric system. For example, each student may start out with a perfect score of 100 for each status metric, with each driving event corresponding to each metric further reducing this score by an amount based on the severity of the driving event, the severity being determined as previously discussed with reference to FIG. 3. The driver feedback score may be calculated using any suitable technique, such as any of the techniques as described in commonly-assigned co-pending U.S. application Ser. No. 13/844,090, for example.

VI. An Example Feedback Display Method

Figure 5:
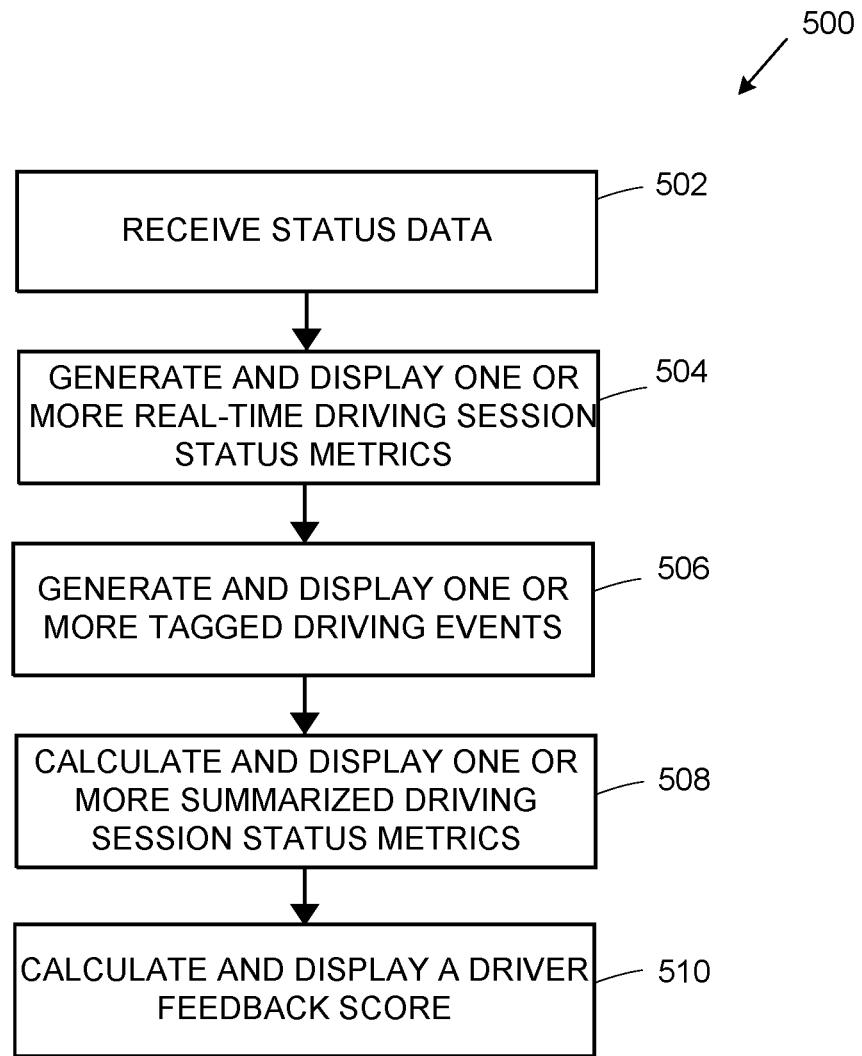
FIG. 5 illustrates an example feedback display method 500 in accordance with an exemplary aspect of the present disclosure.

FIG. 5 illustrates an example feedback display method 500 in accordance with an exemplary aspect of the present disclosure. In the present aspect, method 500 may be implemented by any suitable device, such as device 110, device 111, on-board computer 114, and/or server 140, as shown in FIG. 2, for example. In an aspect, method 500 may be performed by one or more processors, applications, and/or routines, such as any suitable portion of controller 204, applications 230, and/or routines 234, for example, as shown in FIG. 2.

Method 500 starts when a first device receives status data from a second device (block 502). The first and second devices could include, for example, device 110 and device 111, respectively. This status data could include, for example, status data corresponding to a status of driver 106 and/or a status of vehicle 108, for example, as described with reference to FIG. 1. In an aspect, the status data may be generated at device 110 using any relevant sensor and send to device 111 (block 502). Additionally or alternatively, method 500 may include device 110, server 140, and/or on-board computer 114 generating the status data via any relevant sensors and device 110 relaying status data to device 111, in an aspect (block 502). In an aspect, the first device may receive the status data using any suitable communication device, such as I/O circuit 216 and/or communication unit 220, for example, as shown in FIG. 2.

Method 500 may include the first device generating and displaying one or more real-time status metrics based on the received status data (block 504). This could include, for example, the first device generating one or more calculated values and/or conditions interpreted from the status data, as shown and described with reference to FIG. 1. In various aspects, the first device may generate the real-time status metrics using any suitable processing device, application, and/or routine, such as controller 204, feedback application 237, and/or feedback generation and display routine 239, for example, as shown in FIG. 2. In an aspect, method 500 could include the status metrics being displayed in any suitable portion of a suitable display, such as portion 304 and/or 306, for example, as shown in FIG. 3 (block 504).

Method 500 may include generating and displaying one or more tagged driving events (block 506). This may include, for example, the first device generating one or more tagged driving events based on one or more status data values exceeding one or more thresholds, as previously discussed with reference to acceleration, braking, and cornering status metrics displayed within portion 308 of screenshot 300, as shown in FIG. 3 (block 506). This may also include, for example, a driving instructor manually entering a tagged driving event and an accompanying description, which is in turn displayed on the map as a custom tagged driving event, as previously discussed with reference to the manually entered tagged driving event with an accompanying description of "no complete stop at intersection of Elm and Main", within portion 308 of screenshot 300, as shown in FIG. 3 (block 506).

Once the driving session has ended, either via automatic detection thereof of via a user selecting an appropriate option, such as "end" as displayed in portion 302 of screenshot 300, as shown in FIG. 3, method 500 includes calculating and displaying one or more summarized driving session status metrics (block 508). Again, in accordance with such aspects, the first device may determine whether the driving session has ended could be using any suitable processing device, application, and/or routine, such as controller 204, feedback application 237, and/or feedback generation and display routine 239, for example, as shown in FIG. 2.

Figure 4B:
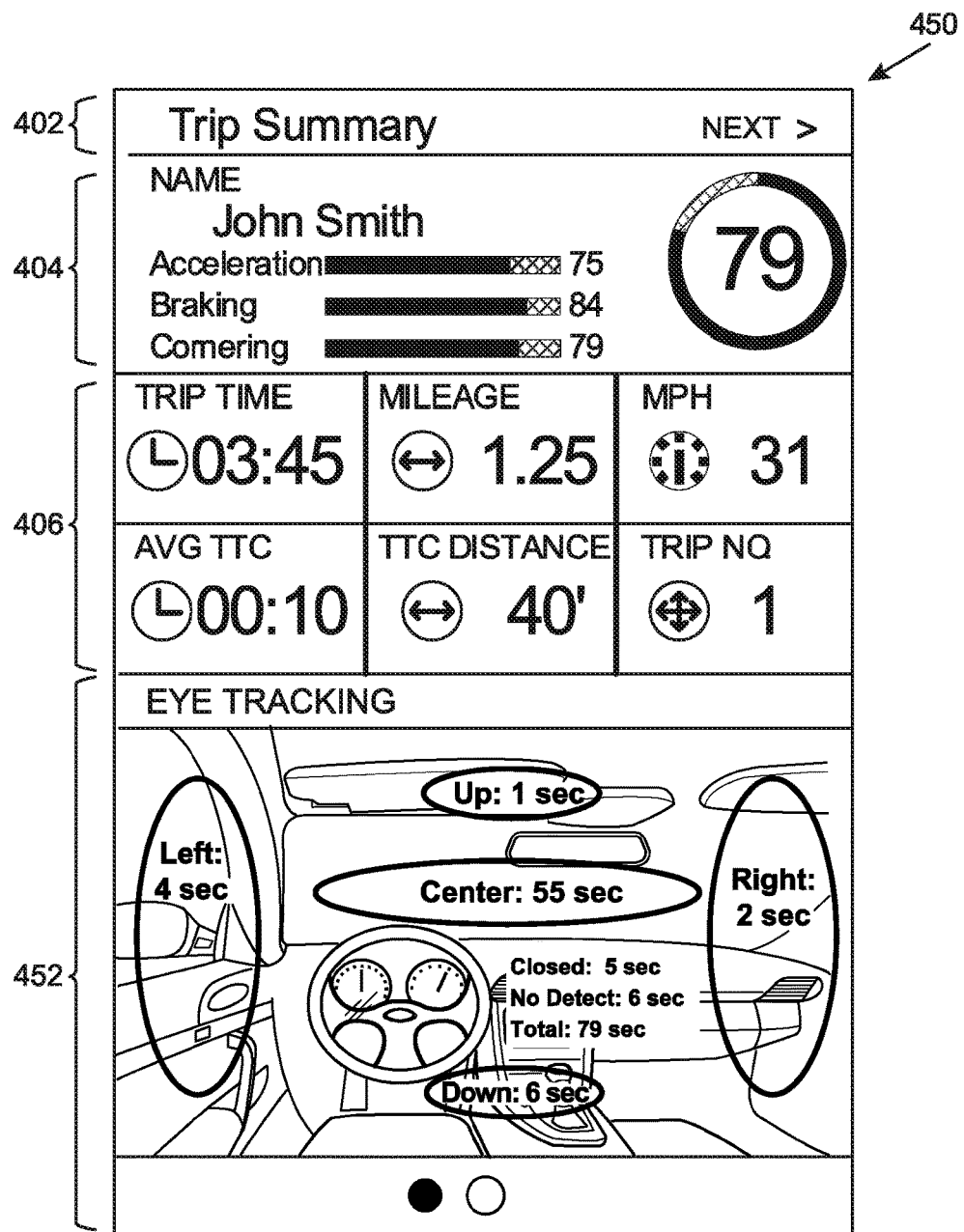
FIG. 4B illustrates an example screenshot 450 of a device used to display a driving session report after a driving session has been completed in accordance with an exemplary aspect of the present disclosure.

The summarized driving session status metrics could include, for example, one or more status metrics as shown in portion 406 of screenshots 400 and 450 of FIGS. 4A and 4B, respectively (block 508). In addition, the summarized driving session status metrics could include, for example, the tagged driving events as shown in portion 408 of screenshot 400 (block 508). To provide yet another example, the summarized driving session status metrics could include an eye tracking report as shown in portion 452 of screenshot 450 (block 508). In various aspects, the first device may generate the summarized driving session status metrics using any suitable processing device, application, and/or routine, such as controller 204, feedback application 237, and/or feedback generation and display routine 239, for example, as shown in FIG. 2.

Method 500 may include calculating and displaying a driver feedback score (block 510). In various aspects, the first device may calculate and display the driver feedback score using any suitable processing device, application, and/or routine, such as controller 204, feedback application 237, and/or feedback generation and display routine 239, for example, as shown in FIG. 2. In an aspect, method 500 could optionally include, for example, a driver feedback score being generated based on any suitable algorithm and/or routine, as previously discussed with reference to FIGS. 4A and 4B (block 510). In an aspect, method 500 could include the driver feedback score being generated and displayed in any suitable portion of a suitable display, such as portion 404, for example, as shown in FIGS. 4A-4B (block 510).

Although the disclosure uses various examples of a student driver and driving instructor using the disclosed feedback application, various aspects may apply to other users as well. For example, various aspects include using the feedback application in conjunction with drivers being retested, reassessed, and/or rehabilitated, and is not limited to only new driving students.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter of the present disclosure.

Additionally, certain aspects are described herein as including logic or a number of components or modules. Modules may constitute either software modules (e.g., code stored on a machine-readable medium) or hardware modules. A hardware module is tangible unit capable of performing certain operations and may be configured or arranged in a certain manner. In example aspects, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In some cases, a hardware module may include dedicated circuitry or logic that is permanently configured (e.g., as a special-purpose processor, such as a field programmable gate array (FPGA) or an application-specific integrated circuit (ASIC)) to perform certain operations. A hardware module may also include programmable logic or circuitry (e.g., as encompassed within a general-purpose processor or other programmable processor) that is temporarily configured by software to perform certain operations. It will be appreciated that the decision to implement a hardware module in dedicated and permanently configured circuitry or in temporarily configured circuitry (e.g., configured by software) may be driven by cost and time considerations.

Accordingly, the term hardware should be understood to encompass a tangible entity, be that an entity that is physically constructed, permanently configured (e.g., hardwired), or temporarily configured (e.g., programmed) to operate in a certain manner or to perform certain operations described herein. Considering aspects in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware and software modules can provide information to, and receive information from, other hardware and/or software modules. Accordingly, the described hardware modules may be regarded as being communicatively coupled. Where multiple of such hardware or software modules exist contemporaneously, communications may be achieved through signal transmission (e.g., over appropriate circuits and buses) that connect the hardware or software modules. In aspects in which multiple hardware modules or software are configured or instantiated at different times, communications between such hardware or software modules may be achieved, for example, through the storage and retrieval of information in memory structures to which the multiple hardware or software modules have access. For example, one hardware or software module may perform an operation and store the output of that operation in a memory device to which it is communicatively coupled. A further hardware or software module may then, at a later time, access the memory device to retrieve and process the stored output. Hardware and software modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example aspects, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example aspects, the processor or processors may be located in a single location (e.g., within a home environment, an office environment or as a server farm), while in other aspects the processors may be distributed across a number of locations.

The one or more processors may also operate to support performance of the relevant operations in a "cloud computing" environment or as a SaaS. For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example aspects, the one or more processors or processor-implemented modules may be located in a single geographic location (e.g., within a home environment, an office environment, or a server farm). In other example aspects, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" or a "routine" is a self-consistent sequence of operations or similar processing leading to a desired result. In this context, algorithms, routines and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one aspect" or "an aspect" means that a particular element, feature, structure, or characteristic described in connection with the aspect is included in at least one aspect. The appearances of the phrase "in one aspect" in various places in the specification are not necessarily all referring to the same aspect.

Some aspects may be described using the expression "coupled" and "connected" along with their derivatives. For example, some aspects may be described using the term "coupled" to indicate that two or more elements are in direct physical or electrical contact. The term "coupled," however, may also mean that two or more elements are not in direct contact with each other, but yet still co-operate or interact with each other. The aspects are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, condition A or B is satisfied by any one of the following: A is true (or present) and B is false (or not present), A is false (or not present) and B is true (or present), and both A and B are true (or present).

In addition, use of the "a" or "an" are employed to describe elements and components of the aspects herein. This is done merely for convenience and to give a general sense of the description. This description should be read to include one or at least one and the singular also includes the plural unless it is obvious that it is meant otherwise.

Upon reading this disclosure, those of skill in the art will appreciate still additional alternative structural and functional designs for providing an interface for receiving data during a driving session and displaying feedback data through the disclosed principles herein. Thus, while particular aspects and applications have been illustrated and described, it is to be understood that the disclosed aspects are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method, comprising:
receiving, at a first mobile computing device located in a vehicle during a driving session, status data from a second mobile computing device located in the vehicle, the status data being generated by the second mobile computing device,
generating, at the first mobile computing device by one or more processors, a tagged driving event when the status data indicates an occurrence of an event that is relevant to driving performance; and
concurrently displaying, at the first mobile computing device, a greater number of different types of driving session information than the second mobile computing device is capable of concurrently displaying,
wherein the driving session information is based upon the status data and includes (i) a map of the driving session route and the tagged driving event at a location along the driving session route where the tagged driving event occurred, (ii) a driver status, or (iii) a vehicle status.

2. The method of claim 1, wherein the status data is indicative of one or more of (i) the vehicle's acceleration, (ii) the vehicle's movement while braking, or (iii) the vehicle's movement while cornering.

3. The method of claim 2, further comprising:
calculating, by one or more processors, status metric values associated with each of (i) the vehicle's acceleration, (ii) the vehicle's movement while braking, and (iii) the vehicle's movement while cornering, based upon the status data; and
calculating, by one or more processors, a driver feedback score based upon the status metric values.

4. The method of claim 1, wherein the act of concurrently displaying the different types of driving session information comprises:
concurrently displaying the different types of driving session information in real time to provide feedback during the driving session.

5. The method of claim 1, wherein the driver status comprises one or more of:
driver eye movement;
a direction of a driver's gaze;
driver head position; or
a driver biometric.

6. The method of claim 1, wherein the vehicle status comprises one or more of:
vehicle road speed;
vehicle engine speed;
a time to collision (TTC);
a lane position of the vehicle;
vehicle light status; or
vehicle braking status.

7. The method of claim 1, wherein the act of generating the tagged driving event comprises:
generating a custom tagged driving event in response to receiving a user input, and
wherein the act of concurrently displaying the different types of driving session information includes displaying the custom tagged driving event at a location along the driving session route corresponding to a location of the vehicle when the user input was received.

8. A system, comprising:
a first mobile computing device configured to generate status data during a driving session while located in a vehicle; and
a second mobile computing device configured to (i) receive the status data from the first mobile computing device during the driving session, (ii) generate a tagged driving event when the status data indicates an occurrence of an event that is relevant to driving performance, and (iii) concurrently display a greater number of different types of driving session information than the second mobile computing device is capable of concurrently displaying,
wherein the driving session information is based upon the status data and includes (i) a map of the driving session route and the tagged driving event at a location along the driving session route where the tagged driving event occurred, (ii) a driver status, or (iii) a vehicle status.

9. The system of claim 8, wherein the status data is indicative of one or more of (i) the vehicle's acceleration, (ii) the vehicle's movement while braking, or (iii) the vehicle's movement while cornering.

10. The system of claim 9, wherein the second mobile computing device is further configured to calculate status metric values associated with each of (i) the vehicle's acceleration, (ii) the vehicle's movement while braking, and (iii) the vehicle's movement while cornering, based upon the status data, and to calculate a driver feedback score based upon the status metric values.

11. The system of claim 8, wherein the second mobile computing device is further configured to concurrently display the different types of driving session information in real time to provide feedback during the driving session.

12. The system of claim 8, wherein the driver status comprises one or more of:
driver eye movement;
a direction of a driver's gaze;
driver head position; or
a driver biometric.

13. The system of claim 8, wherein the vehicle status comprises one or more of:
vehicle road speed;
vehicle engine speed;
time to collision (TTC);
a lane position of the vehicle;
vehicle light status; or
vehicle braking status.

14. The system of claim 8, wherein the second mobile computing device is further configured to generate a custom tagged driving event in response to receiving a user input, and to concurrently display the different types of driving session information including displaying the custom tagged driving event on the map of the driving session at a location of the vehicle when the user input was received.

15. A first mobile computing device, comprising:
  a processor configured to generate a tagged driving event when status data from a second mobile computing device located in a vehicle indicates an occurrence of an event that is relevant to driving performance, the status data being generated by the second mobile computing device; and
  a display configured to concurrently present a greater number of different types of driving session information than the second mobile computing device is capable of concurrently presenting,
  wherein the driving session information is based upon the status data and includes (i) a map of the driving session route and the tagged driving event at a location along the driving session route where the tagged driving event occurred, (ii) a driver status, or (iii) a vehicle status.

16. The first mobile computing device of claim 15, wherein the status data is indicative of one or more of (i) the vehicle's acceleration, (ii) the vehicle's movement while braking, or (iii) the vehicle's movement while cornering, and
  wherein the processor is further configured to calculate status metric values associated with each of (i) the vehicle's acceleration, (ii) the vehicle's movement while braking, and (iii) the vehicle's movement while cornering, based upon the status data, and to calculate a driver feedback score based upon the status metric values.

17. The first mobile computing device of claim 15, wherein the display is further configured to concurrently present the different types of driving session information in real time to provide feedback during the driving session.

18. The first mobile computing device of claim 15, wherein the driver status comprises one or more of:
  driver eye movement;
  a direction of a driver's gaze;
  driver head position; or
  a driver biometric.

19. The first mobile computing device of claim 15, wherein the vehicle status comprises one or more of:
  vehicle road speed;
  vehicle engine speed;
  time to collision (TTC);
  a lane position of the vehicle;
  vehicle light status; or
  vehicle braking status.

20. The first mobile computing device of claim 15, wherein the processor is further configured to generate a custom tagged driving event in response to receiving a user input, and to concurrently present the different types of driving session information including presenting the custom tagged driving event at a location along the driving session route corresponding to a location of the vehicle when the user input was received.

* * * * *